United States Patent [19]
Nakajima et al.

[11] Patent Number: 5,214,737
[45] Date of Patent: May 25, 1993

[54] OPTICALLY OPERATED ACTUATOR

[75] Inventors: Naomasa Nakajima, Chofu; Yoshihiro Naruse, Ichikawa; Mitsuhiro Ando, Tokyo; Tomokimi Mizuno, Chiryu, all of Japan

[73] Assignee: Aisin Seiki Kabushiki, Kariya, Japan

[21] Appl. No.: 764,677

[22] Filed: Sep. 25, 1991

[30] Foreign Application Priority Data

Sep. 26, 1990 [JP] Japan ................. 2-256400

[51] Int. Cl.⁵ .................. G02B 6/00; F16K 27/00
[52] U.S. Cl. ..................... 385/147; 385/900; 385/115; 251/11; 126/569; 337/298; 337/327
[58] Field of Search ............ 385/31, 38, 115, 147, 385/900; 251/11; 126/417; 337/298, 306, 320, 327

[56] References Cited

U.S. PATENT DOCUMENTS

| | | | |
|---|---|---|---|
| 3,847,547 | 11/1974 | Delgendre et al. | 337/300 X |
| 4,065,593 | 12/1977 | Peterson | 126/449 X |
| 4,259,593 | 3/1981 | Proud et al. | 337/331 X |
| 4,758,695 | 7/1988 | Sanford et al. | 337/320 X |
| 4,821,997 | 4/1989 | Zdeblick | 251/11 |
| 4,940,896 | 7/1990 | Hagins et al. | 250/338.3 |
| 4,943,032 | 7/1990 | Zdeblick | 251/11 |

OTHER PUBLICATIONS

A resume announcing a conference of the Japan Society of Robot, held Sep. 20-22, 1988, pp. 275-276.
Journal of Japan Society of Robot, vol. 5, No. 2, pp. 3-17, published Apr., 1987 (the last page being and English abstract).

*Primary Examiner*—Akm E. Ullah
*Attorney, Agent, or Firm*—Finnegan, Henderson, Farabow, Garrett & Dunner

[57] ABSTRACT

An actuator includes a closed space defined by a deformable member in which an amount of thermally expansible gas is filled. In the closed space, there is also a substance which changes the light into the heat. A control device is set to establish the supply of the light into the closed space. Upon turning-on of the control device, the substance changes the supplied light into the heat, resulting in that the resultant heat brings the expansion of the gas. Thus, the member is brought into deformed condition. The deformation can be used as a force for operating a specific element.

8 Claims, 11 Drawing Sheets

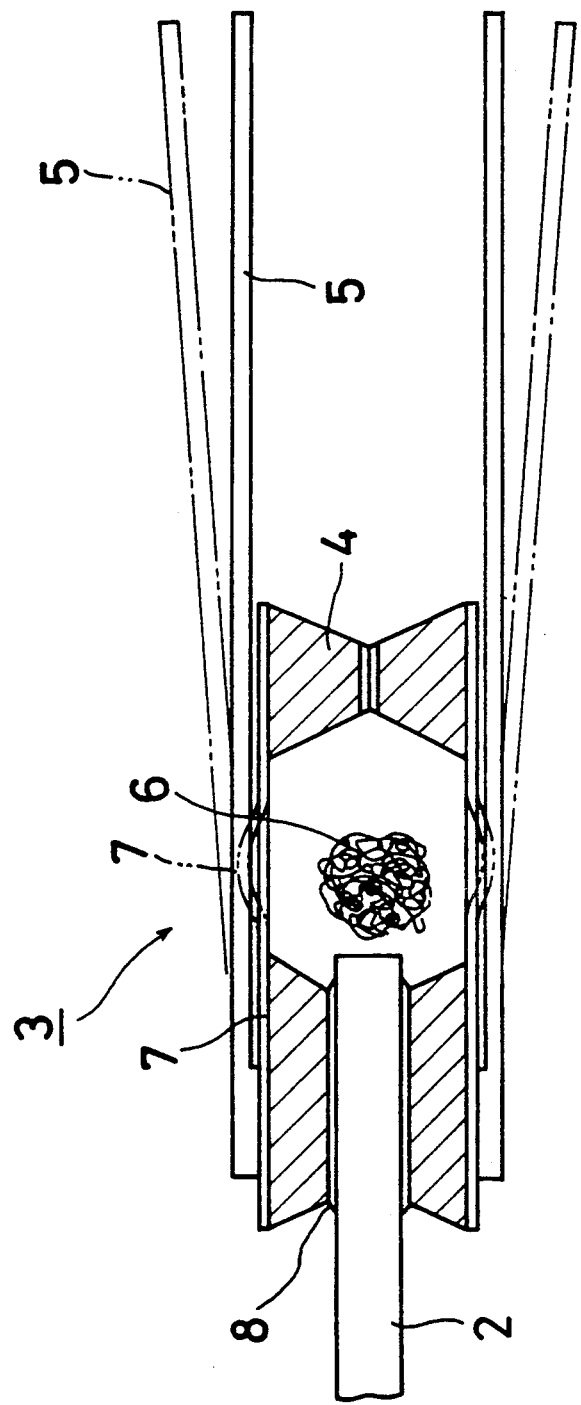

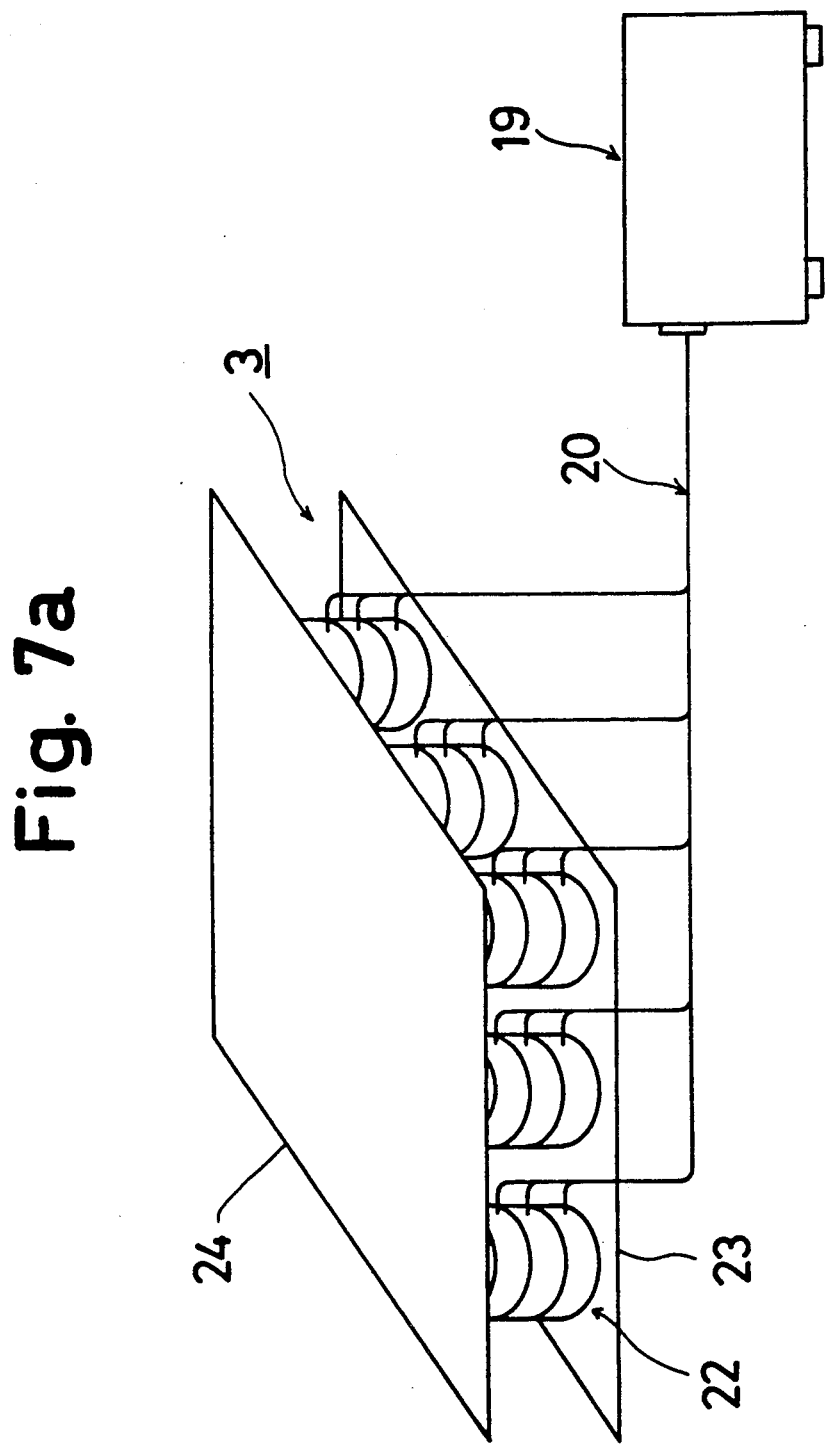

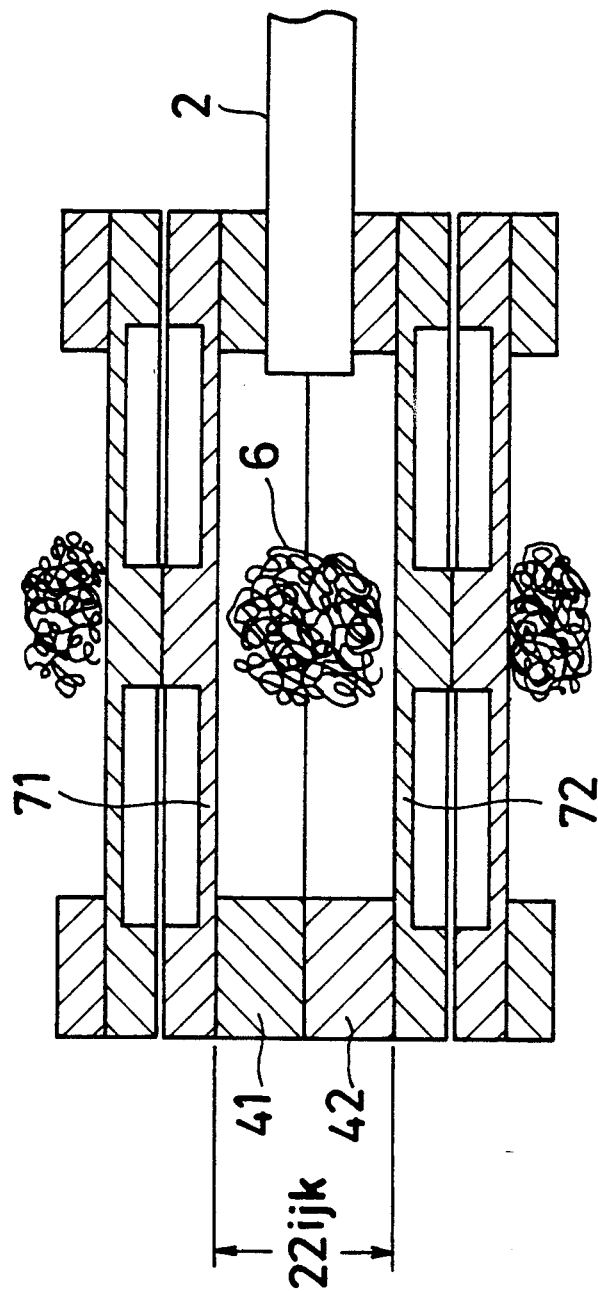

OPTICALLY OPERATED ACTUATOR

BACKGROUND OF THE INVENTION

The present invention relates to an actuator and in particular to an actuator for operating a relatively minute device such as a catheter, a manipulator for operating the cell or a manipulator for operating a robot to be used in a narrow space.

Such actuator is required to be of a miniaturized configuration as possible and to be under easy, safety control.

However, reviewing the conventional actuators, no actuator is found which complies with the foregoing two requirements.

SUMMARY OF THE INVENTION

It is, therefore, a principal object of the present invention to provide an actuator which complies with the foregoing requirements.

Another object of the present invention is to provide an actuator which can be made into a miniaturized configuration as possible and which is easy and safety in its control.

In order to attain the foregoing objects, an actuator is comprised of a closed space defined by deformable member, an amount of thermally expansible fluid in the closed space, a substance for changing the light into the heat which is accommodated in the closed space and control means for establishing the supply of the light into the closed space.

BRIEF DESCRIPTION OF THE DRAWINGS

FIG. 4 is an elevational cross-sectional view of an actuator;

FIG. 7a is a perspective view of another embodiment of an actuator according to the present invention; and FIG. 7b is an enlarged elevational cross sectional view of an actuator shown in FIG. 7.

DETAILED DESCRIPTION OF THE PREFERRED EMBODIMENTS

Figure 1:
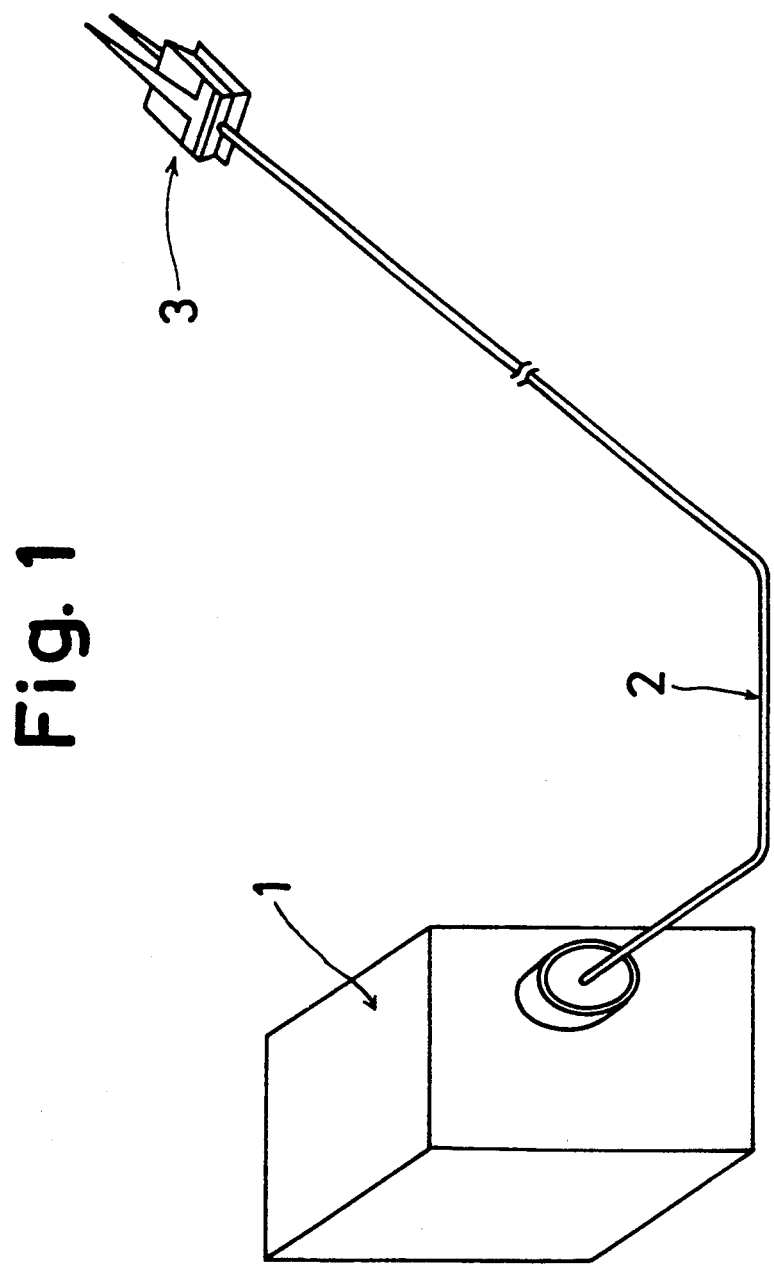
FIG. 1 is a perspective view of one embodiment of an actuator according to the present invention.

Referring first to FIG. 1 in which an appearance of the first embodiment of a thermally operated actuator 3 according to the present invention, the actuator 3 is in optical connection or communication with a controller 1 through an optical fiber 2.

Figure 2:
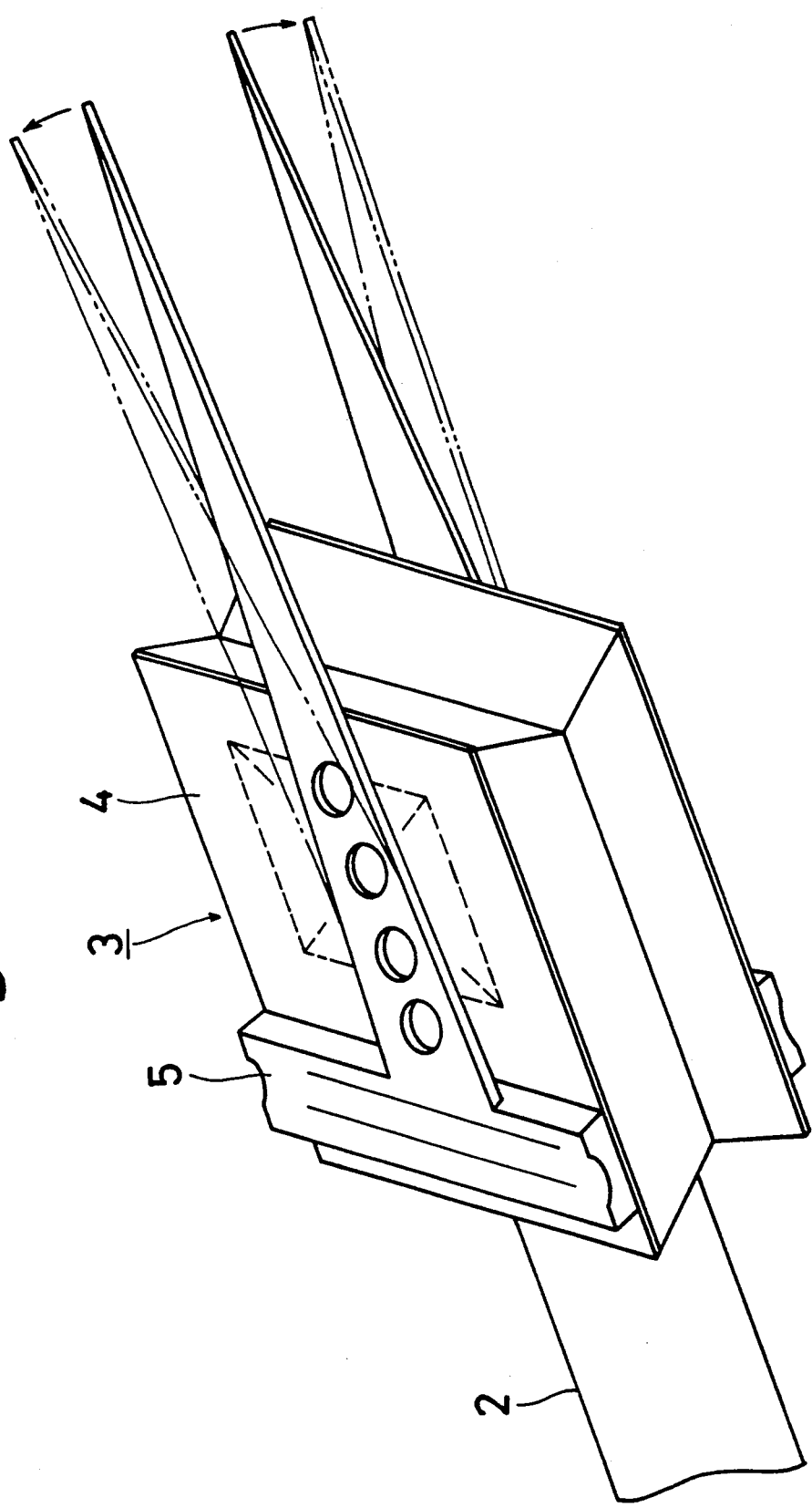
FIG. 2 is an perspective view of a main portion of an actuator in FIG. 1.
Figure 3:
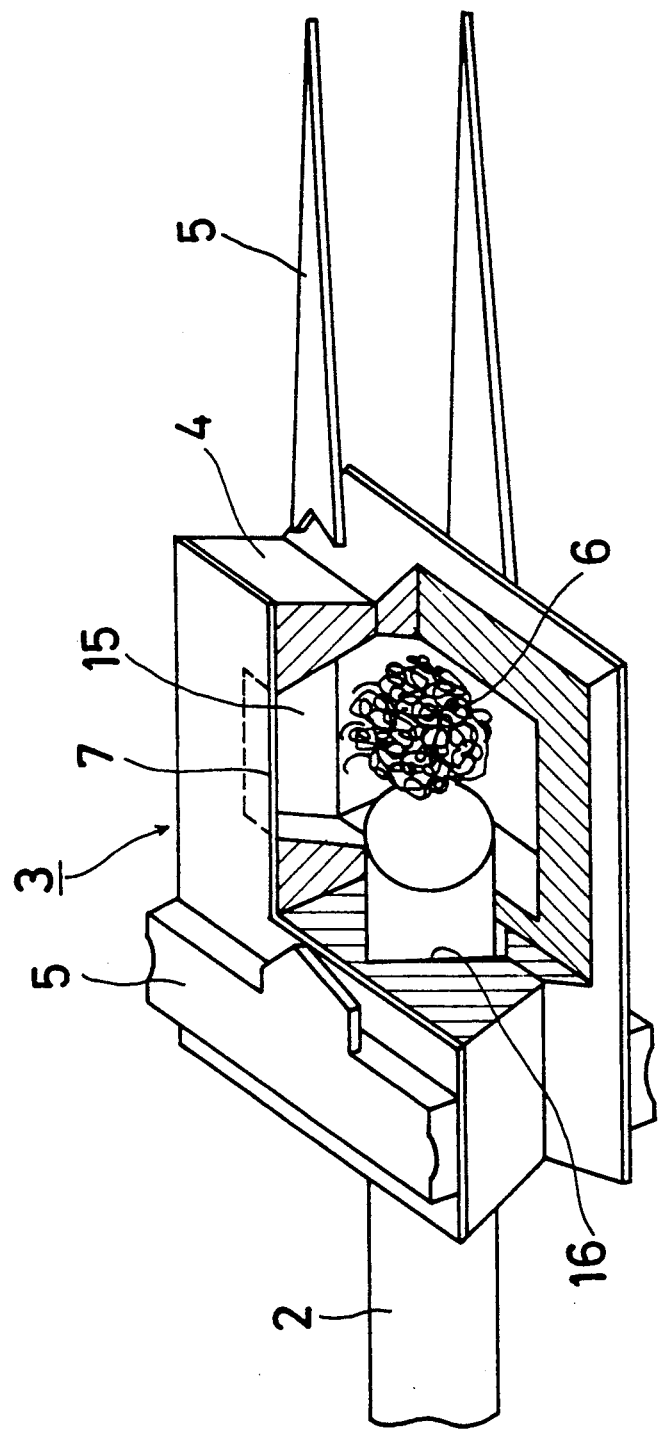
FIG. 3 is an illustrative view of an actuator.

As shown in FIGS. 2, 3 and 4, the actuator 3 includes a pair of levers 5 and 5 for holding a minute object (not shown), a diaphragm 4 by which each of the levers 5 and 5 is brought into the opened position shown in real line and vice versa and the optical fiber 4 through which optical rays are beamed into an inner space 15 of the diaphragm 4. A distal end of the optical fiber 2 is extended through a notch 16 into the inner space 15 in which an light-heat conversion substance such as a carbon fiber 6 is accommodated for the effective conversion of the light energy into the heat energy. The diaphragm 4 has an expansion membrane 7 and a slight gap is defined between the lever 5 and the membrane 7.

A gap between the optical fiber 2 and the diaphragm 4 is filled with a sealing member 8.

The controller includes a light source (not shown) and when the source is turned on light comprising plural rays is emitted or beamed therefrom into the inner space 15 of the actuator 3 through the optical fiber 2. The majority of the resulting light is absorbed in the substance 6, which generates heat therein. Thus, the temperature of the substance is increased thereby inflating the mass of gas in the inner space 15. This brings the increase of the pressure within the inner space 15 with the result that the membrane 7 is expanded in the outward direction as shown in two-dotted line in FIG. 4. The resulting membrane 7 brings each lever 5 in the outward direction and right side of each lever is brought into opened condition shown in two-dotted line. When the light source is turned off, the temperature within the inner space 15 is automatically lowered thereby shrinking the mass of gas in the inner space 15. Thus, the membrane 7 is shrunk again with resulting that each lever 5 is returned to its original or initial position as shown in real line.

As apparent from the foregoing, for holding the minute object, it is only required to turn off the light source after positioning the minute object between the levers 5 and 5 each of which is opened position as a result of the turning-on of the light source. For releasing the minute object which has been once held by the levers 5 and 5, only the turning on of the light source is required.

A description on re how to constitute the actuator 3 will be detailed hereinafter.

Figure 5A:
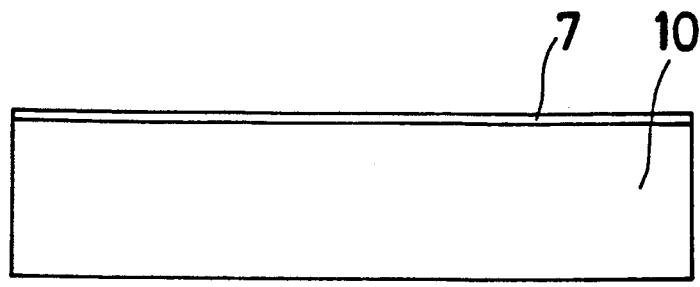
FIGS. 5a through 5l and 6a through 6c show sequential steps for producing an actuator.

(1) First of all, as shown in FIG. 5a, the membrane 7 in the form of a thin film 7 of $SiO_2$ on a surface of a silicon base plate 10.

Figure 5B:
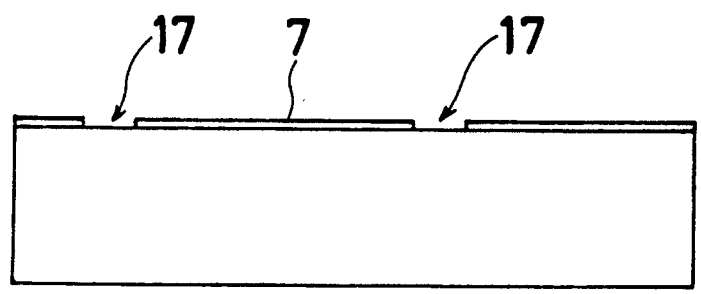

(2) A plurality of windows 17 are formed in the membrane 7 for the separation of the diaphragm tip 4 by means of photolithography as shown in FIG. 5b.

Figure 5C:
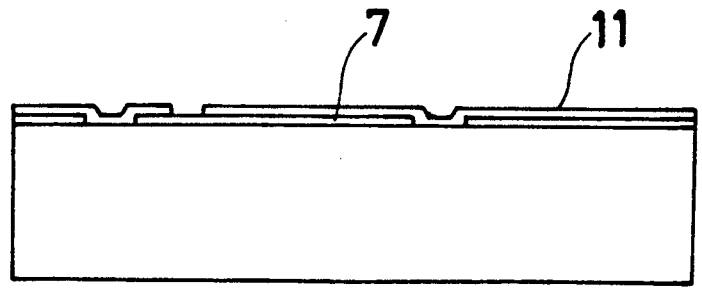

(3) In order to define the gap between the diaphragm 4 and each lever 5, an idle filler membrane 11 is formed by means of the vacuum evaporation method (FIG. 5c).

Figure 5D:
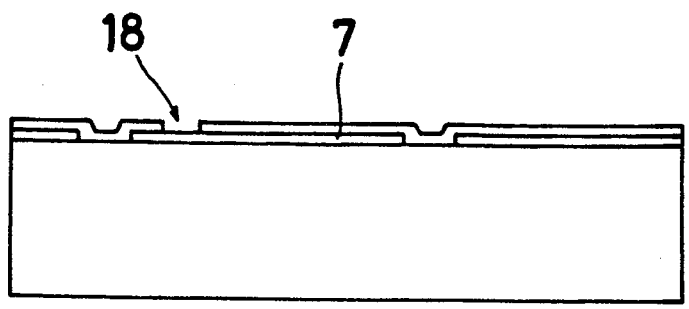

(4) A window 18 is formed at a portion of the idle membrane 11 for the connection of a root portion of each lever 5 with the diaphragm 4 by means of the photolithography (FIG. 5d).

Figure 5E:
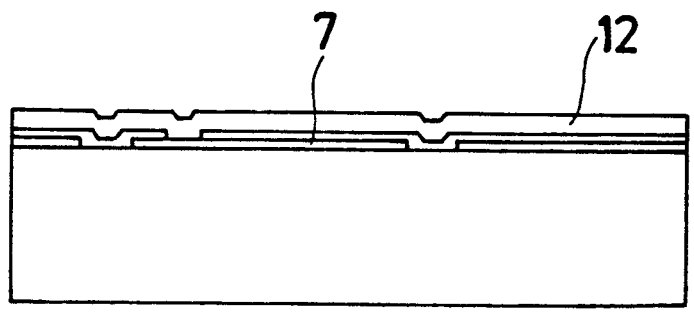

(5) On the idle membrane 11, a substance of NiCr as a raw material of each lever 5 is formed by the sputtering (FIG. 5e).

Figure 5F:
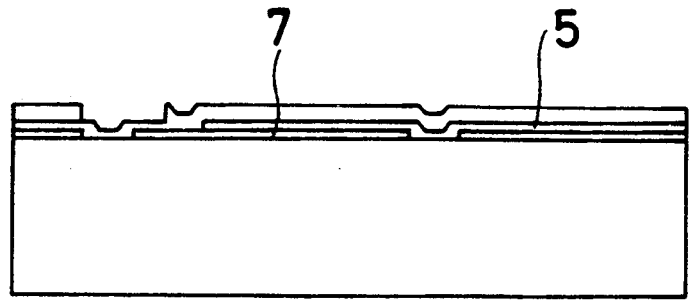

(6) Each lever 5 is formed by means of photolithography (FIG. 5f).

Figure 5G:
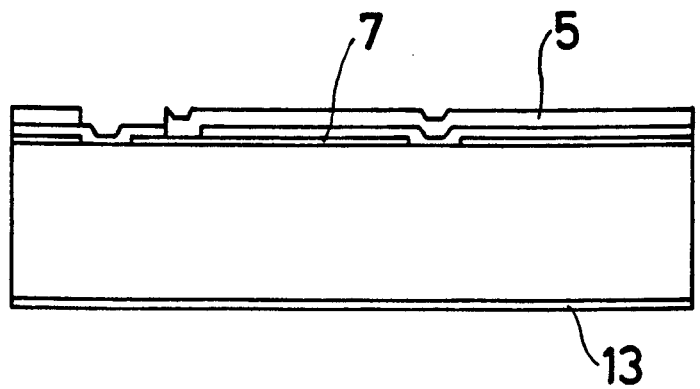

(7) A thin film of $SiO_2$ is formed on a back side of the plate 10 which is used as a mask material for the etching process (FIG. 5g).

Figure 5H:
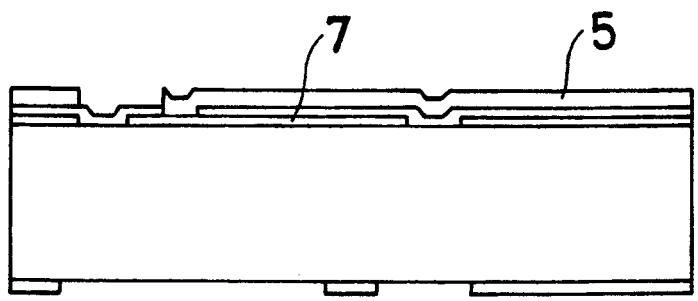
Figure 5I:
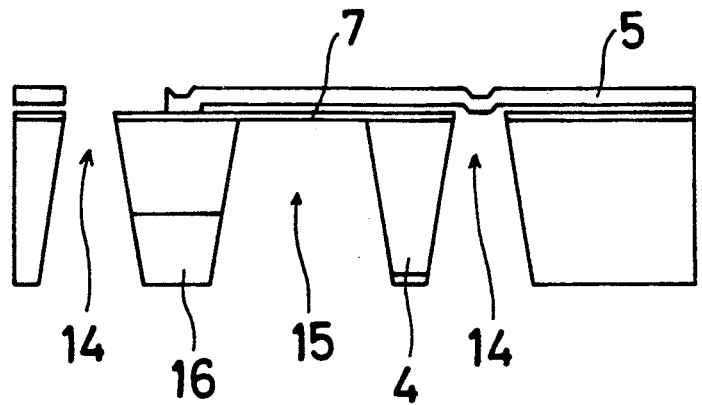

(8) After positioning with rear patterns, the thin film 13 at the back side of the plate 10 is brought into window-opened condition (FIG. 5h).

Figure 5J:
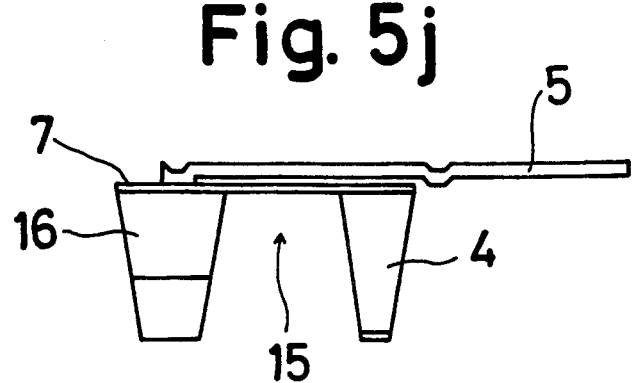

(9) Notches 14, 15 and 16 are formed in the plate 10 by means of an aeolotropy etching method (FIGS. 5a and 5j).

Figure 5K:
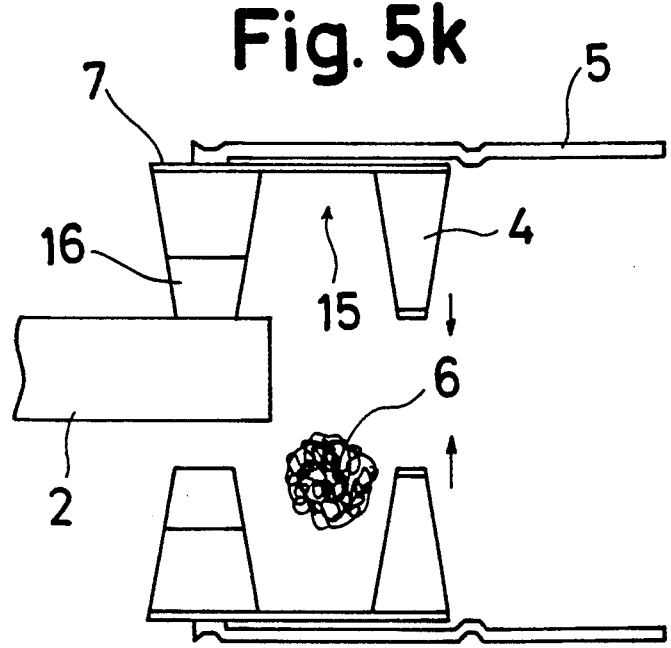
Figure 5L:
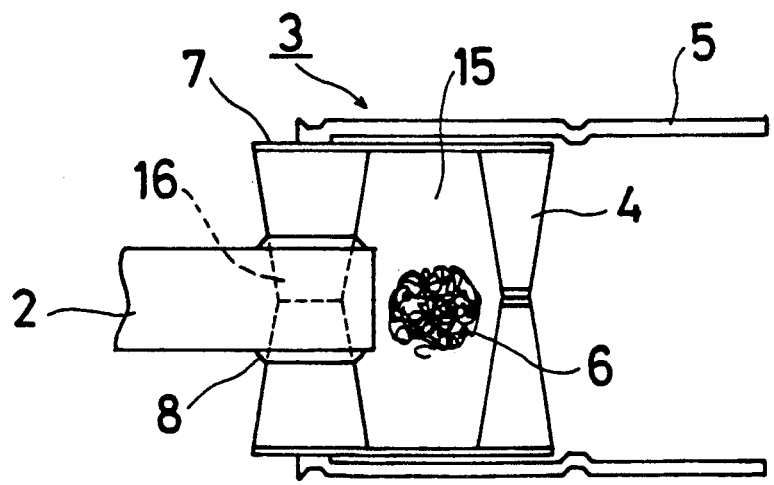

(10) A pair of the resultant members each of which is obtained through the processes of the foregoing steps 1 through 9 are coupled with each other so that the carbon filer 6 may be in the inner space 15 between both members and the distal end of the optical fiber 2 may be held between the members via the sealing member 8 (FIG. 5k and 5l).

The rating (kind, pressure and other conditions) of gas to be filled within the inner space 15 is to be set at the foregoing step (10).

As the raw material of the thin film 7, instead of SiO$_2$, a specific metal or a synthetic resin is available.

Figure 6A:
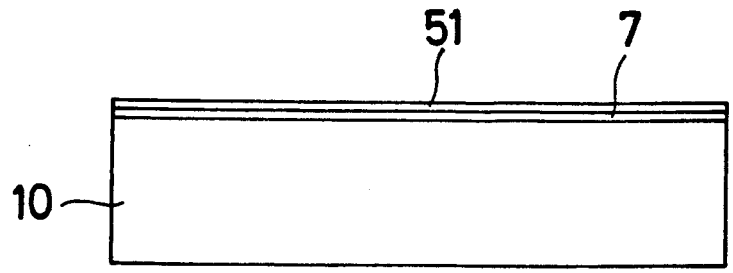
Figure 6B:
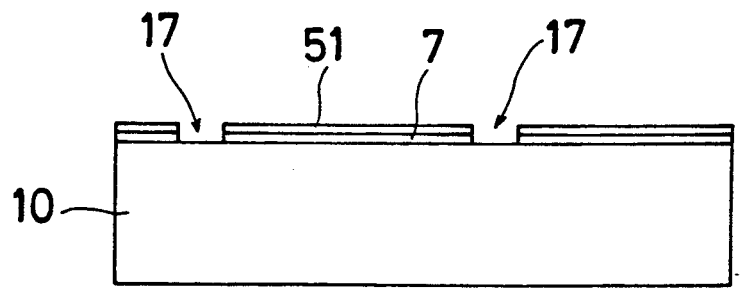
Figure 6C:
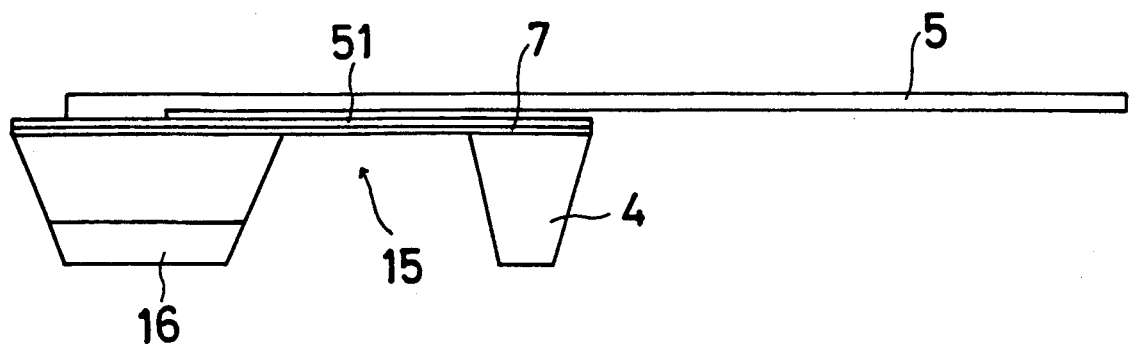

In the second embodiment of the present invention, the thin film 7 of SiO$_2$ is covered with a metal membrane 41 whose raw material is same as that of each lever 5. This is performed by means of the sputtering method (FIG. 6a) after the foregoing process (1) and the window 17 is formed as shown in FIG. 6b corresponding to FIG. 5b. Thereafter, the foregoing processes (3) through (10) are established for the treatment of the resultant. In the second embodiment, the thickness of the thin film 7 is out of matter.

The third embodiment of the present invention is shown in FIG. 7a. In this embodiment, a plurality of diaphragm elements are arranged in the three-dimensional manner between a base plate 23 and an upper plate 24 which is of flexibility as an operating element, and each diaphragm element 22 is in optical communication via corresponding optical fiber 2 with a control unit 19.

In FIG. 7b, there is illustrated the cross-sectional configuration of the diaphragm element 22$ijk$ in the enlarged-scale. The optical fiber 2 is held between silicon rings 41 and 42 and an upper side opening (a lower side opening) is closed by a membrane 71 (72) which is of high flexibility. Within an inner space defined by the membranes 71 and 72 and rings 41 and 42, there is accommodated the carbon fiber 6. Three constructed diaphragm element each of which is thus constructed are stacked in the vertical direction, and a set of the resulting three-storied elements are arranged in two-dimensional directions in the form of 3×3. Each element is set to be inflated (shrunk) upon establishment (interruption) of the supply of light thereto, which enables the deformation or movement of the upper plate 24 in any directions.

Obviously, numerous modifications and variations of the present invention are possible in light of the above teachings. It is therefore to be understood that within the scope of the appended claims, the invention may be practised otherwise than as specifically described herein.

What is claimed is:

1. An optically operated actuator comprising:
   a body having a closed space therein containing an amount of thermally expansible fluid, the body including a deformable portion movable in varying degree in the outward direction of the body upon expansion of the fluid;
   an external actuation member connected to the deformable portion of the body;
   light-to-heat converting means accommodated in the closed space; and
   control means for establishing the supply of light into the closed space, the control means being in the form of an element separated from the body and terminated in the closed space.

2. An optically operated actuator in accordance with claim 1, wherein the light-to-heat converting means is in the form of a plurality of mutually entangled fiber shaped substances.

3. An optically operated actuator in accordance with claim 2, wherein most of outer surfaces of the substances are exposed to the expansible fluid.

4. An optically operated actuator in accordance with claim 2, wherein the substances are formed into a substantially spherical configuration.

5. An optically operated actuator in accordance with claim 2, wherein each of the substances is a carbon fiber.

6. An optically operated actuator in accordance with claim 1, wherein the control means has an optical fiber terminating in the closed space after passing through the body.

7. An optically operated actuator comprising:
   a body having a closed space therein containing an amount of thermally expansible fluid, the body being provided with a pair of opposed deformable portions, both of which are deformable in varying degrees in opposite outward direction of the body upon expansion of the fluid;
   a pair of members connected to the pair of deformable portions of the body, respectively, and operated so that the distance between the members is increased when the fluid is expanded;
   light-to-heat converting means in the closed space; and
   control means, separated from the body, for establishing the supply of light into the closed space.

8. An optically operated actuator comprising:
   a body having a closed space therein containing an amount of thermally expansible fluid, the body being provided with a deformable portion movable in varying degree in outward direction of the body upon expansion of the fluid;
   an external actuation member connected to the deformable portion of the body;
   light-to-heat converting means in the closed space; and
   control means, for establishing the supply of light into the closed space, the control means being in the form of an element separated from the body.

* * * * *

UNITED STATES PATENT AND TRADEMARK OFFICE
CERTIFICATE OF CORRECTION

PATENT NO. : 5,214,737

DATED : May 25, 1993

INVENTOR(S) : Naomasa NAKAJIMA et al.

It is certified that error appears in the above-identified patent and that said Letters Patent is hereby corrected as shown below:

Claim 7, column 4, line 28, "direction" should read --directions--.

Signed and Sealed this

Fourteenth Day of December, 1993

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,214,737
DATED : May 25, 1993
INVENTOR(S) : Naomasa NAKAJIMA et al.

It is certified that error appears in the above-identified patent and that said Letters Patent is hereby corrected as shown below:

On the title page, Item [73]:
The assignee, "Aisin Seiki Kabushiki, Kariya, Japan"

should read --Aisin Seiki Kabushiki Kaisha, Kariya, Japan--.

Signed and Sealed this

First Day of March, 1994

BRUCE LEHMAN

*Attest:*

*Attesting Officer*      *Commissioner of Patents and Trademarks*